United States Patent [19]

DeCello et al.

[11] Patent Number: 5,117,370

[45] Date of Patent: May 26, 1992

[54] DETECTION SYSTEM FOR CHEMICAL ANALYSIS OF ZINC PHOSPHATE COATING SOLUTIONS

[75] Inventors: Michael J. DeCello, Dearborn Heights; LeRoy C. Westwood, Redford, both of Mich.

[73] Assignee: Ford Motor Company, Dearborn, Mich.

[21] Appl. No.: 288,648

[22] Filed: Dec. 22, 1988

[51] Int. Cl.⁵ .................... C23C 22/05; G06F 15/20
[52] U.S. Cl. .................................. 364/497; 364/502; 148/253; 148/262
[58] Field of Search .............. 364/497, 499, 502; 73/61 R, 61 LM, 19.07; 427/8; 204/1 T; 148/253, 262

[56] References Cited

U.S. PATENT DOCUMENTS

| | | | |
|---|---|---|---|
| 2,872,353 | 2/1959 | Metheny | 427/8 |
| 3,532,519 | 10/1970 | Hirohata et al. | 427/8 |
| 3,934,054 | 1/1976 | Schmeling et al. | 427/8 |
| 3,942,546 | 3/1976 | Radd et al. | 73/19.07 |
| 4,053,743 | 10/1977 | Niemi | 364/500 |
| 4,055,751 | 10/1977 | Bussmann et al. | 364/500 |
| 4,096,301 | 6/1978 | Slominski et al. | 427/437 |
| 4,276,323 | 6/1981 | Oka et al. | 204/1 T |
| 4,286,965 | 9/1981 | Vanhumbeeck et al. | 427/8 |
| 4,310,563 | 1/1982 | Oka et al. | 427/8 |
| 4,350,717 | 9/1982 | Araki et al. | 427/8 |
| 4,353,933 | 10/1982 | Araki et al. | 427/8 |
| 4,623,554 | 11/1986 | Kaschok et al. | 427/8 |
| 4,624,857 | 11/1986 | Dahms | 427/8 |
| 4,692,346 | 9/1987 | McBride et al. | 427/8 |
| 4,699,081 | 10/1987 | Mack | 427/8 |
| 4,707,377 | 11/1987 | Capwell et al. | 427/8 |
| 4,707,378 | 11/1987 | McBride et al. | 427/8 |
| 4,717,431 | 1/1988 | Knaster et al. | 148/262 |
| 4,788,086 | 11/1988 | Matsuda | 148/262 |
| 4,880,476 | 11/1989 | Matsuda et al. | 148/262 |
| 4,941,930 | 7/1990 | Charles et al. | 148/262 |

Primary Examiner—Parshotam S. Lall
Assistant Examiner—Ellis B. Ramirez
Attorney, Agent, or Firm—Lorraine S. Melotik; Roger L. May; Randolph A. Smith

[57] ABSTRACT

This invention is directed to a detection system for the quantitative analysis of chemical components of an aqueous phosphate conversion-coating bath, in particular, to a system for determining the concentration of zinc ions, phosphate ions, nitrite ions, and the pH of a purified sample of the bath. Optionally, the concentrations of other ions which might be present such as fluoride ions and nickel ions also can be determined. This detection system is preferably an automated on-line detection system employing X-ray fluorescence analysis, and flow injection analysis comprising specific ion electrodes and a flow through colorimeter or spectrophotometer. The automated, on-line detection system comprises computer means for automating said detection system and the computer means may be adapted for recording the resultant determinations and maintaining the chemical components at chosen concentrations in the bath.

23 Claims, 1 Drawing Sheet

DETECTION SYSTEM FOR CHEMICAL ANALYSIS OF ZINC PHOSPHATE COATING SOLUTIONS

TECHNICAL FIELD

This invention is related to a detection system for analyzing respective quantities of chemical components of a zinc phosphate conversion-coating bath.

BACKGROUND OF THE INVENTION

Zinc phosphate conversion-coatings have been applied to car and truck bodies for well over 50 years to provide corrosion protection and an adhesion base for paint. These coatings, in conjunction with the electrocoat (E-coat) primer, provide most of the corrosion protection for cold rolled steel and virtually all of the paint adhesion properties to both cold rolled steel and galvanized steel. The zinc phosphate conversion-coatings are deposited by electrochemical reaction of the metal substrate with an acidic, aqueous solution of metal phosphates carefully adjusted to a pH generally between 2.7 and 3.2. A typical, widely used, commercial zinc phosphate solution for automotive uses having this pH range contains hydrogen, zinc, and nickel cations; monohydrogen and dihydrogen phosphates; nitrate and fluoride anions; and soluble phosphate complexes of zinc and nickel. An accelerator, such as nitrite, which facilitates the solution of the iron surface and removal of $H_2$, is continuously added to the solution in order to accelerate the electrochemical reaction during the phosphating operation.

Optimum phosphate coatings are only obtained if the components of the phosphate bath are maintained within the specific narrow limits designated for each constituent. As metallic parts are immersed or sprayed in large scale phosphating operations, the coating deposition process removes nickel, zinc, and phosphate from a bath and reduces bath acidity. Constituent monitoring and replenishment must keep pace with the depletion rate. Current industrial practice is to monitor only three bath parameters: free acid (FA), total acid (TA), and the nitrite accelerator, and to do so by manual titration. The bath is then replenished based on these parameters. The concentration of bath constituents such as nickel, zinc, and fluoride, all of which effect the coating quality, are maintained by addition of a mixed ion concentrate based on the free and total acid levels being monitored. The mixed ion concentrate is prepared assuming a depletion rate that is a unique function of the change in free and total acid. This assumption is generally not valid since all the components are not depleted at a constant rate because coating composition varies with the line speed, temperature, metal surface reactivity, metal mix, and other factors. From studies of such baths, we have found that the total phosphate result, currently derived from total acid count, is not accurate due to the presence of phosphate-metal complexes. Additionally, we have found some wide fluctuations in the zinc and nickel levels even though the current control methods show the baths to be operating within the process specification for free acid, total acid and nitrite.

It has been found that to insure that precise bath compositions are maintained it is necessary to quantitatively analyze the following zinc phosphate bath parameters: PH, total phosphate (mathematically related to total phosphorus and total acid), nitrite, and zinc concentrations. The concentrations of other component ions such as nickel and fluoride, when used, preferably also need to be quantitatively analyzed. Based upon such analysis, a precise bath composition can be maintained, a rigorous requirement for the application of consistently high quality coatings from phosphate baths in use at the present time.

DISCLOSURE OF THE INVENTION

The invention is directed to a detection system and a method for quantitative analysis of chemical components of an aqueous phosphate conversion-coating bath, which system comprises: means for purifying a sample of the aqueous phosphate conversion-coating bath to form a test fluid consisting essentially of an aqueous solution of ionic species; means for determining the concentration of zinc ions in the test fluid, means for determining the concentration of phosphate ions in the test fluid, means for determining the pH (i.e., the hydrogen ion concentration), and means for determining the concentration of the nitrite ions in the test fluid. Since most automotive, zinc phosphate baths used to coat cold rolled steel and galvanized steel prior to painting comprise nickel and fluoride in addition to the ions mentioned above, the detection system of this invention also preferably additionally comprises means for determining the concentration of nickel ions in the test fluid and means for determining the concentration of fluoride ions in the test fluid. The system may further comprise conduit means to provide the test fluid to the purifying means and/or the various determining means and computer means for recording the determined concentrations.

Preferably, the detection system is an automated, on-line detection system having conduit means providing the bath sample to a purifying means and other conduit means providing the test fluid to various determining means of the types described above, the purifying means and determining means being automated means, i.e., equipment which perform the desired operations automatically. Such a preferred automated, on-line detection system would automatically (1) subject a bath sample to purification, (2) subsequently subject the purified bath sample (test fluid) to analytical testing to determine the concentration of various ions, and then (3) make the results of the determinations available to one requiring such determinations, e.g., to a technician monitoring the bath. The determinations could be provided to the computer for recording and the computer could be adapted to make them available to an interested party.

More preferably, according to such a detection system, the means for determining the concentration of the zinc ions, the nickel ions (when present) and the phosphate ion comprises X-ray fluorescence analysis; the means for determining the pH and the means for determining the concentration of the fluoride ions (when present) comprises flow injection analysis employing specific ion electrodes; and the means for determining the concentration of the nitrate ions comprises flow injection analysis employing a spectrophotometer or colorimeter with a flow-through cell. Preferably, the purifying means comprises an ultrafilter system.

The invention in another aspect is directed to a method for the automated, on-line quantitative analysis described above. This method comprises the steps of: automatically providing a sample of the bath to a purifying means by a conduit means, automatically purifying the sample to form a test fluid consisting essentially of an aqueous solution of ionic species, and automatically providing the test fluid by other conduit means to determining means and thereby automatically determining the concentration of zinc ions in the test fluid, of phosphate ions present in the test fluid, of the pH of the test fluid, and nitrite ions in the test fluid. The method further comprises automatically carrying out the steps of the method by means of a computer. Optionally, the method may further comprise automatically determining the concentration of fluoride and nickel ions in the test fluid.

Advantageously, the chemical detection system described above, particularly the preferred automated system, employs a X-ray analyzer system with a flow through cell for the detection of the zinc ions, nickel ions (when present), and phosphate ion concentrations. This allows for direct analysis; no regents are required other than the calibration standards. In addition, the phosphate result obtained is a measure of the total phosphorous and, therefore, more accurate than the total acid as an expression of the orthophosphate concentration. Use of the particular embodiments of analysis as described herein, particularly the use of flow injection analysis techniques using specific ion electrodes for determination of pH (as a measure of free acid) and fluoride ion concentration, and a spectrophotometer (or colorimeter) with a flow through cell for determination of the nitrite concentration are advantageous because of the inherent simplicity, speed, and reproducibility of such analysis techniques.

DESCRIPTION OF PREFERRED EMBODIMENTS

Figure 1:
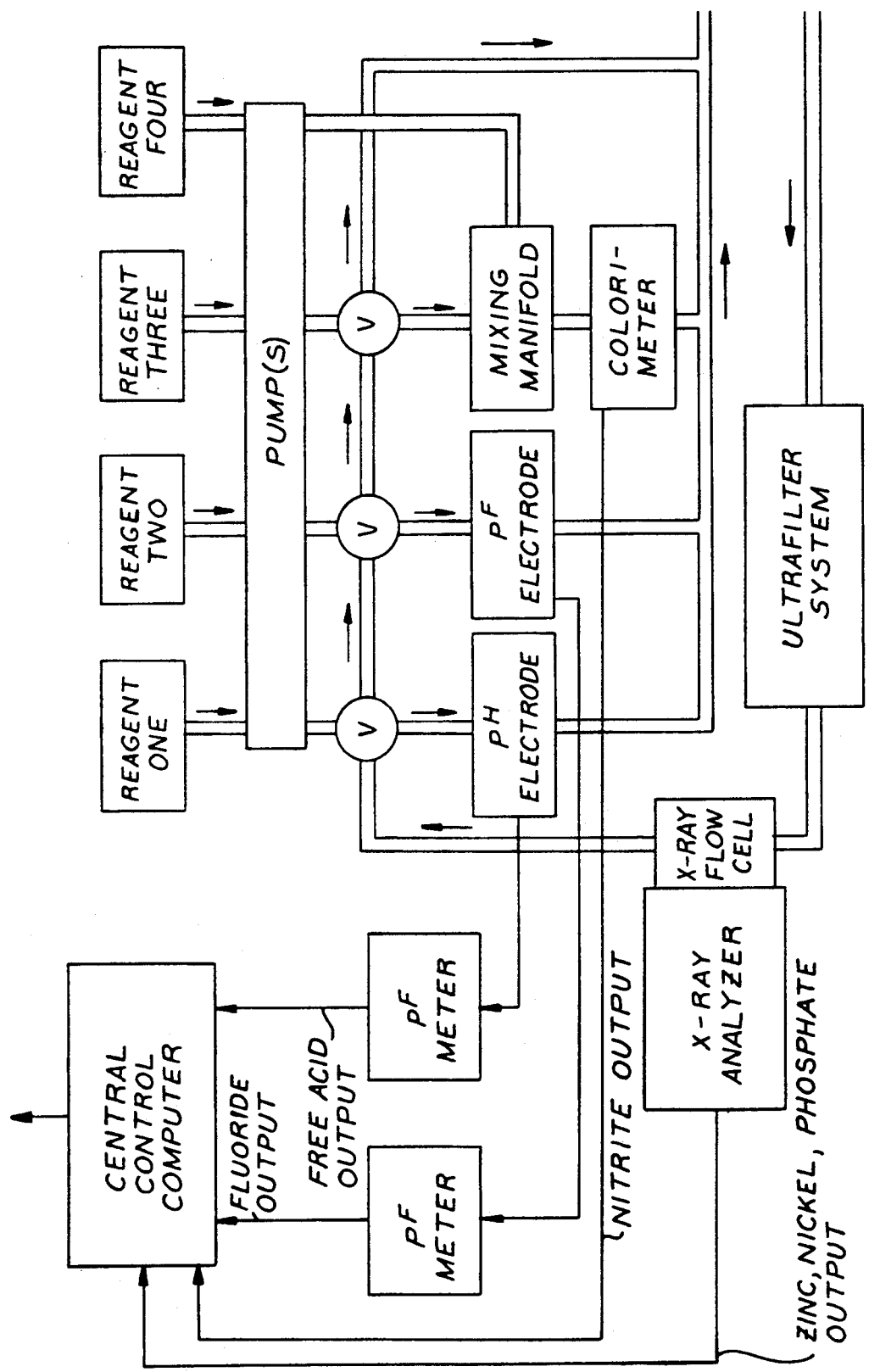
FIG. 1 is a schematic representation of an embodiment of an automated, on-line chemical detection system according to the present invention.

As disclosed above, this invention is directed to a chemical detection system for analysis of aqueous phosphate conversion-coating baths, most particularly of the bath type used in automotive applications. This invention is not however limited to analysis or automotive type baths. Such automotive baths typically comprise an acidic, aqueous solution of metal phosphates, for example, phosphates of zinc and nickel as well as nitrates or sulfates thereof, fluorides, nitrites, chloride, peroxide, etc. Often a portion of the nickel layer forming metals may be replaced by cations of one or more divalent, layer-forming metals selected from the group consisting of cobalt, manganese, and magnesium. According to the present invention, the system comprises a means for purifying a sample portion of a zinc phosphate conversion-coating bath to provide a test fluid consisting essentially of ionic species. This test fluid is subsequently subjected to qualitative analysis of various chemical components thereof, including zinc ions, phosphorate, PH, and nitrite ions. Optionally, the test fluid additionally may be subjected to qualitative analysis of other chemical components which may be present, such as nickel ions, fluoride ions and other ions such as those mentioned above.

The means for purifying the bath sample is intended to remove substantially any sludge present in the bath sample so that it only contains (an aqueous solution of) ionic species. Such purification may be done, for example, by well known purification means such as ultrafiltration, settling techniques, normal filtration techniques, centrifuge techniques, etc. Other useful purification techniques would be apparent to those skilled in the art in view of the present disclosure. A conduit means may be employed to provide the bath sample to the purifying means.

The means for determining the concentration of the various chemical components described above can be made by any analytical method or instrument, a variety of such methods and instruments being well known to those skilled in the art. Exemplary of such methods are titration (manual or instrumental), ion chromatography, spectro-photometric determinations, fluorometric determinations, electrochemical determinations, colorimetric determinations, atomic absorption and emission determinations, etc. The detection system may further comprise a conduit means for providing the test fluid to the various determining means which quantitatively analyze chemical components of the test fluid as desired. Preferably, the detection system further comprises a computer means connected to the determining means for recording the results of the quantitative analyses carried out by the determining means. Such computer means could be programmed to provide information useful to maintain the various bath components at chosen (desired) levels. This computer means could be programmed to provide information useful in making up a concentrate of the various components, which concentrate could be used to replenish the bath (in those cases where depletion of the bath components is taking place in a consistent fashion). This computer means also could be used (by itself or in combination with other computer means) in another instance to control the addition of chemicals to the bath as would be necessary to maintain the chemical components of the bath as chosen concentrations.

According to a preferred embodiment of the invention, the detection system is an automated, on-line detection system comprising conduit means for providing a sample of the aqueous phosphate conversion-coating bath to an automated means for purifying the sample to form the test fluid. Such an automated, on-line system further comprises other conduit means to provide the test fluid to automated means for determining the concentrations of the various components. Such an automated system would include a computer means for automating the various means of the system. The computer means of the detection system could be adapted, e.g., to record the determined concentrations of the various chemical components of the test fluid. The automated detection system is described in greater detail below.

FIG. 1 shows an embodiment of the preferred automated, on-line chemical detection system. This system advantageously can withstand the chemically harsh environments provided by the bath components and provide an accurate, detailed analysis of the aqueous phosphate conversion-coating baths with a minimum of maintenance. According to this embodiment, a bath sample is automatically brought through a feed line to an automated means for purifying the bath sample, in this embodiment being an ultrafiltration system. The ultrafiltration system removes the sludge (solid materials) from the bath sample and leaves only ionic materials in the sample. While the ultrafiltration system is preferred for use in the automated, on-line detection system, other purification means may suitably be used in the system. Selection of the optimal automated purification means for use in the automated, on-line system will be within the skill of those in the art in view of the present disclosure.

METAL ION AND PHOSPHATE DETERMINATION

In the embodiment of the automated, on-line detection system shown in FIG. 1, the purified bath sample, herein called the "test fluid", passes through a preferred means for automatically measuring the concentration of metal ions and phosphate ion: an X-ray analyzer employing an X-ray flow cell. In particular, the preferred X-ray analyzer is an X-ray fluorescence analyzer which is capable of measuring the concentration of ions of metals such as zinc and nickel, and phosphate ion (as a measure of phosphorous and total acid). Thus, in this embodiment of the invention, the means for measuring the concentration of the zinc ion, the means for measuring the concentration of the nickel ions and the means for measuring the concentration of the phosphate ion is one means, i.e., an X-ray fluorescence analyzer employing an X-ray flow cell. In addition, this analyzer could be adapted to measure the concentration of other metal ions like manganese, cobalt, etc. should that be desired. The X-ray analyzer system according to this preferred embodiment includes X-ray sources, a detector, and an X-ray computer which would control the start up and operation of the analyzer, translation of signals from the detector for mathematical analysis, as well as provide the results of the analysis to a central control computer (shown in FIG. 1).

Exemplary of an X-ray analyzer which is well suited for automated, on-line application and may be used according to the present invention is an ASOMA X-ray Fluorescence Analyzer Model 8660 (trademark, ASOMA Instruments, Austin, Tex.) equipped with a continuous flow-through cell. This analyzer uses low intensity radioactive sources rather than an X-ray tube which requires high voltage and water Cooling. A Cd-109 source can be used for nickel and zinc ion determinations (or preferably a Cm-244 source) while Fe-55 can be used for phosphate. A neon detector can be used for both sources. Other detectors can be used, e.g., argon or xenon. This analyzer can also detect other metal ions, should that be desired, by using these sources or other sources specific for the particular metal ion determination desired. The polypropylene flow-through cell window thickness of 0.5 mils and a count time of about 180 seconds appeared optimal for obtaining precise and accurate concentration results. A microprocessor may be included in the system to control the instrument calibration and subsequent sample analysis. Drift, often a problem in rapid X-ray fluorescence analysis, may be minimized by a user selected time delay that allows the instrument to stabilize itself between analyses.

Calibration and testing of the above particularly described X-ray analyzer equipment used in the preferred embodiment was carried out as follows. A commercial phosphating formulation concentrate, Bonderite 411G, from Parker+Amchem (Madison Heights, Mich.) was analyzed by Induction Coupled Plasma Optical Emission Spectroscopy (ICP-OES) and Ion Chromotography (IC) and used as a standard. This concentrate was diluted with distilled water to 10 different dilution levels. One of these samples was diluted to the level of a phosphating bath at the Wixom Assembly Plant of Ford Motor Company and is called herein, "Wixom Sample".

Analysis of the Wixom Sample by ICP-OES and IC gave 6.53 g/l $PO_4$, 1.53 g/l Zn, and 0.38 g/l Ni.

Calibration standards for testing of the X-ray analyzer used in the preferred embodiment consisted of the 10 different dilution levels of the 411G concentrate. The calibration procedure consists of establishing computer files containing the element named, atomic number, sample concentration, units of measure, and count time for each source. Standards are then pumped through the flow cell at the rate of 500 milliliters/minute, the instrument response for each element recorded and associated with each inputted concentration. Techniques of linear and non-linear regression are employed using software provided with the ASOMA analyzer to develop calibration curves relating instrument response to concentration of the elements. The use of such techniques will be understood by those skilled in the art in view of the present disclosure. The precision of the calibration is established using multiple analyses of each standard.

FLOW INJECTION ANALYSIS

According to the preferred embodiment of this invention shown in FIG. 1, after the test fluid is subjected to X-ray analysis it is next subjected to flow injection analysis using specific ion electrodes for determination of the pH and pF, that is, the determination of the concentration of the hydrogen ion and fluoride ion, respectively, and to flow injection analysis using a colorimeter or spectrophotometer for determination of the nitrite ion concentration. Flow injection analysis is a technique for automating manual analytical procedures. It is based upon the injection of a liquid sample into a flowing, non-segmented carrier stream at various points in time. According to this analysis technique, often, the stream often contains another reagent added to modify the sample. The injected sample of test fluid forms a zone that is transported through a flow-through cell. The cell contains a detector that monitors changes in absorbance, electrode potential, or other physical parameters of the stream as the sample plug of injected test fluid passes the detector that is always monitoring the carrier fluid.

While not used in the particular preferred embodiment of FIG. 1, flow injection analysis systems are commercially available. Such systems generally comprise peristaltic pumps, injection valves, and tubes that can be programmed to remove a small sample of liquid from a process (e.g., a bath), mix it with appropriate amounts of reactive reagents, and then inject it into a flowing carrier stream for presentation to the detector. Such commercially available systems generally contain a variable wavelength flow-through detector run by a microprocessor programmable controller. Such instruments are not preferred in this invention since they do not meet the ruggedness and low maintenance requirements of on-line, industrial applications.

While flow injection analysis (using e.g., commercial instruments of the preferred unique system of FIG. 1) can be used to continuously determine the concentration of various bath components, it has been found satisfactory for excellent bath maintenance to only intermittently determine the required ion concentrations, generally about 4 times per hour. This invention is not however limited to intermittent sampling, nor any particular number of determinations/time. Selection of the optimal sampling type and number of (if intermittent) will be within the skill of one in the art in view of the present disclosure.

In the preferred embodiment of this invention shown in FIG. 1, the flow injection analysis system was newly designed which comprises positive displacement pumps and "slider" type four-way injection valves. The positive displacement pumps were of a rotary/piston design and were obtained from Fluid Metering, Inc., Oyster Bay, N.Y. and were used for delivery of carrier and reagent solutions. Pumps of this type were chosen because of their inherent ability to deliver accurate and consistent volumes of solution. In addition, they require far less maintenance than the more commonly used peristaltic pumps. The four way slider valve was obtained from Omnifit Ltd., Atlantic Beach, N.Y. This type of valve allows for an extremely consistent volume of sample to be delivered for each analysis. In the case of the nitrite determination, the system further comprises a mixing manifold. The mixing manifold was custom fabricated to provide the efficient mixing of the reagents with minimal longitudinal dispersion of the sample stream. The operation of the pumps and "slider" valves are controlled by a computer interface. Optionally, any commercially available mixing manifold could be used in the system as would be apparent to one skilled in the art in viewing for present disclosure.

According to the preferred embodiment of the online detection system shown in FIG. 1, the pH and pF are measured by specific ion "gel" type combination electrodes fitted into the flow-through cells (as shown in FIG. 1). Such electrodes are available, for example, from Orion Research Incorporated, Cambridge, Mass. While this type of electrode has been found preferable in the present invention flow injection analysis system, the detector for the PH and pF is not limited to such electrodes. The combination electrodes used according to the Preferred embodiments for determination of PH and PF had rapid electrode response and also good recovery of the base line. Other detectors, including other types of electrodes, which would be useful in the present invention will be apparent to those skilled in the art in view of the present disclosure. The nitrite ion concentration is measured by a spectrophotometer, i.e., by a colorimetric analysis technique. Other means for nitrite determination which could be suitably used in the preferred flow injection analysis system will be apparent to those skilled in the art in view of the present disclosure.

The flow injection analysis techniques as outlined herein and shown in FIG. 1 were preferably selected for pH, pF, and nitrite ion determinations because, advantageously, it was found that they are inherently simple, rapid and reproducible. For example, a basic difficulty in the use of glass electrodes to continuously measure pH in phosphating solutions in the presence of fluoride ion which deteriorates the glass surface. In flow injection analysis, however, the electrode is in contact with the hostile sample for only a few seconds; most of the time the glass sensing surface is in contact with the carrier buffer solution.

pH DETERMINATION

The combination pH "gel" type electrode fitted into the pH determining cell as described above is connected to a pH meter which is standardized at two points with pH2 and PH4 buffers. The pH2 buffer was used as a continuous carrier stream (reagent one in FIG. 1). The meter was recalibrated after connection to the electrode now monitoring this stream. The Wixom sample described herein was then injected into the flowing carrier stream in order to test the PH sensing system. This system was found to provide reproducible pH readings. During use of the detection system shown in FIG. 1, a volume (sample) of the test fluid is injected into the carrier stream (reagent one) by means of the "slider" valves and pumps. The pH of the injected carrier stream is analyzed as it flows through the cell containing the pH combination electrode.

It is possible to obtain rapid response to pH changes using a flow through capillary electrode, a calomel reference electrode, and 30 microliter samples instead of the "gel" type combination electrode described above. The reference electrode, however, requires maintenance of the filling solution. The use of a combination "gel" type pH electrode according to a preferred embodiment of the invention as shown in FIG. 1 simplifies pH measurement since no reagents are required to keep the electrode continuously filled.

Normally, the speed of flow injection analysis comes from using a sufficiently small sample, however, it provides a response which is less than a steady state value. The detector is merely calibrated and a given response is associated with the given amount of sample. The excellent precision of the technique results from injection of exactly the same amount of sample of test fluid or standard and in variance of the carrier flow rate. For pH, a meter response in millivolts is related to the actual pH by the regression calibration. However, if the sample size is increased, it becomes possible to read the actual pH on the meter. Clearly, this slows measurement. However, since it is found that generally four readings per hour of the pH (and other parameters) of the bath (test fluid) are generally sufficient to maintain the bath composition, the use of larger samples is possible. It was generally found that according to the preferred embodiment described herein, a 400 microliter (or more) injection sample of the test fluid causes full pH (and pF) response of the electrodes. The pH values thus obtained are combined with the phosphorous result from X-ray fluorescence in a multiple regression formula to determine the free acid as will be apparent to one skilled in the art in view of the present disclosure.

pF DETERMINATION

A pH 3 buffer that matches the ionic strength of the phosphating solution was spiked with 0, 50 and 100 ppm fluoride for calibration of the pF meter in a normal batch type manner. The combination pF "gel" type electrode mounted in its flow cell as described above is connected to a pF meter which is again calibrated using the unspiked buffer as a carrier and injecting 400 microliters of the fluoride standards. As a test of the pF sensing system, the Wixom standard was analyzed repeatedly and the peaks were recorded. This system was found to provide reproducible pF readings.

According to the preferred embodiment of the invention shown in FIG. 1 in order to analyze for the fluoride concentration, a volume (sample) of test fluid is injected into a carrier buffer buffered at pH 3.0 (reagent two) by means of the "slider" valve and pumps. This injected carrier flows through the cell containing the pF electrode which analyzes for the concentration of the fluoride ion therein. The response on the pF meter in millivolts indicates the free fluoride present based on a calibration curve prepared by injection of several levels of HF into the buffer as described above.

Standard procedures for determination of fluoride ion by specific ion electrodes are directed towards the determination of total fluoride. This requires the presence of total ionic strength buffer in both the samples and standards. The total ionic strength buffer adjusts the dissolved ionic solids to a uniform level, moves the PH to 5.5, at which most of the HF is disassociated, and contains EDTA to complex heavy metals, a source of complication in pH determinations. In the case of the phosphate bath, however, it is only the free fluoride ion concentration at operating conditions that needs to be determined.

As mentioned hereinbefore, fluoride ions are employed in phosphating baths to complex any aluminum ions which might be present since aluminum severely inhibits the phosphating reactions. Fluoride is generally added in the form of fluosilcic acid which partially disassociates to hydrofluoric acid. At the normal operating pH (2.7—3.2) of the phosphate bath, the HF is only slightly disassociated to $F^-$. The situation, therefore, is one of having a reservoir present to provide fluoride ion as needed. The monitoring tasks are simply one of confirming the presence of free $F^-$ at a level sufficient to accomplish the aluminum complexation (generally about 100 ppm). Even in those baths not containing aluminum, fluoride ions are after added to prevent "nubbing" or "white spotting" on galvanized steel. Should the bath not contain fluoride ions, the system could be modified to eliminate the means for measuring the fluoride ion concentration in the test sample as would be apparent to one skilled in the art in view of the present disclosure.

NITRIDE DETERMINATION

As discussed above, the preferred embodiment flow injection analysis system used in the present invention for determination of the nitrite ion concentration (shown in FIG. 1) comprises positive displacement pumps, a "slider" type four-way injection valve, a mixing manifold and a spectrophotometer. Calibration curves for the instrument were constructed and recorded for the analysis by means of standard solutions containing 10, 20, 30, 40, and 50 ppm nitrite and deionized water. A similar set of solutions using the Wixom sample spiked to comparable levels was then analyzed to determine the precision. It was found that the flow injection analysis nitrite determination system provided accurate and reproducible results.

During analysis for nitrite ion concentration by the system of FIG. 1, a volume (sample) of the test fluid is injected into the carrier stream (reagent three) and mixed with reagent four (a modifying reagent) by means of the mixing manifold. The reacted sample is then delivered to a spectrophotometer or colorimeter, e.g., a Model 16A spectrophotometer from Research & Control Labs, Detroit, Mich. The absorbance of the reacted sample is detected at the desired wavelength. In the case of reagent three being an acidic sulfanilamide solution and reagent four being N-(1-naphthyl)ethylenediamine, an azo dye is formed in the analyzed material whose absorbance is measured at 540 mn wavelength.

According to the preferred embodiment of the automated system of FIG. 1, the operation of the pumps and slider valve are controlled by a computer means (central control computer shown in FIG. 1). In addition, the output signals from the spectrophotometer are mathematically manipulated in the software of this computer to provide for an integration of the data curve. Integration of the data curve is preferred over the more commonly used peak height method because this method of data manipulation makes the analysis more robust to fluctuations in reagent flow rates, reagent concentration and tubing flow restrictions (i.e., from reagent crystal buildup in tubing) and makes sample volume the only critical parameter for providing accurate and consistent analyses.

The central control computer can be programmed to run all of the necessary operations not run by the X-ray computer in order to provide a fully automated detection system. For example, as described above the central control computer can control the functioning of the "slider" valves, the pumps, control the operation of the ultrafiltration system, flow rates, wavelength setting, calibrations, the time at which the detection system is to do an analyses of the bath, etc. In addition, this computer can be programmed to record the determined concentrations of the various bath components measured and further adapted to provide information which allows the concentration of the bath components to be maintained at chosen concentrations. Using such information from the analysis of the concentrations of various ions in the bath according to the present invention, the desired concentration of the chemical components may be maintained at optimal levels in different ways. For example, based on such information specifically tailored concentrated mixtures of the various depleted ions can be made, which concentrate can be used to replenish the bath. A concentrate would be ideal for use in those instances where the depletion of the bath components with time is fairly constant so that a concentrate may be suitably employed. In those cases wherein depletion of the ions of the bath has not taken place at a substantially uniform rate, it would be desirable to replenish the bath constituents individually as needed. This may arise in situations wherein the line speed, type of metal being coated, etc., is varying in a relatively short period of time so that depletion is not taking place at a uniform rate.

As would be apparent from the present disclosure, the injected and analyzed carrier fluid (as shown in the drain line below the colorimeter in FIG. 1 by arrows pointing to the right) would be dumped, i.e., not returned to the bath.

In view of this disclosure, many modifications of this invention will be apparent to those skilled in the art. It is intended that all such modifications which fall within the true scope of this invention be included within the terms of the appended claims.

We claim:

1. A detection system for quantitative analysis of chemical components of an aqueous phosphate conversion-coating bath, which detection system comprises:
    means for purifying a sample of said aqueous Phosphate conversion-coating bath to form a test fluid consisting essentially of an aqueous solution of ionic species;
    means for determining the concentration of zinc ions present in said test fluid;
    means for determining the concentration of phosphate ions present in said test fluid;
    means for determining the pH of the test fluid;
    means for determining the concentration of nitrite ions present in said test fluid; optionally, means for determining the concentration of fluoride ions present in said test fluid; and, optionally, means for determining the concentration of nickel ions present in said test fluid.

2. The detection system according to claim 1, wherein said system further comprises means for determining the concentration of cobalt ions present in said test fluid.

3. The detection system according to claim 1, wherein said system further comprises means for determining the concentration of manganese ions present in said test fluid.

4. The detection system according to claim 2, wherein said system further comprises means for determining the concentration of manganese ions present in said test fluid.

5. The detection system according to claim 1, wherein said detection system further comprises conduit means for providing said test fluid to all of the determining means.

6. The detection system according to claim 1, wherein (1) said means for determining said concentration of said zinc ions, (2) said means for determining said concentration of said nickel ions, and (3) said means determining said concentration of said phosphate ions comprises X-ray fluorescence analysis.

7. The detection system according to claim 6, wherein (1) said means for determining said pH, and said means for measuring said concentration of said fluoride ions comprises flow injection analysis employing specific ion electrodes, and (2) said means for determining said concentration of said nitrite ions comprises flow injection analysis employing colorimetric analysis techniques.

8. The detection system according to claim 1, which further comprises a computer means connected to the determining means for recording the determined concentrations of the components of said test fluid and its pH.

9. An automated on-line detection system for quantitative analysis of chemical components of an aqueous phosphate conversion-coating bath, which automated on-line detection system comprises:

conduit means for providing a sample of said aqueous phosphate conversion-coating bath to an automated means for purifying said sample to form a test fluid consisting essentially of an aqueous solution of ionic species; and other conduit means for providing said test fluid to:

automated means for determining the concentration of zinc ions present in said test fluid;

automated means for determining the concentration of phosphate ions present in said test fluid;

automated means for determining the PH of the test fluid;

automated means for determining the concentration of nitrite ions present in said test fluid; optionally, automated means for determining the concentration of nickel ions present in said test fluid; optionally, automated means for determining the concentration of fluoride ions present in said test fluid; and computer means for automating said detection system.

10. The automated on-line detection system according to claim 9, wherein said system further comprises an automated means for determining the concentration of cobalt ions present in said test fluid.

11. The automated on-line detection system according to claim 9, wherein said system further comprises an automated means for determining the concentration of manganese ions present in said test fluid.

12. The automated on-line detection system according to claim 10, wherein said system further comprises an automated means for determining the concentration of manganese ions present in said test fluid.

13. The automated on-line detection system according to claim 9, wherein (1) said automated means for determining said concentration of said zinc ions, (2) said automated means for determining said concentration of said nickel ions, and (3) said automated means for determining said concentration of said phosphate ions comprises X-ray fluorescence analysis.

14. The automated on-line detection system according to claim 9, wherein (1) said automated means for determining said pH, and said automated means for measuring said concentration of said fluoride ions comprises flow injection analysis employing specific ion electrodes, and (2) said automated means for determining said concentration of said nitrite ions comprises flow injection analysis employing colorimetric analysis techniques.

15. The automated on-line detection system according to claim 9, wherein said computer means is adapted for recording the determined concentrations of the components of said test fluid and its pH.

16. The automated on-line detection system according to claim 15, wherein said computer means provides information which allows the concentration of the chemical components of the aqueous phosphate conversion-coating bath to be maintained at chosen concentrations.

17. The automated on-line detection system according to claim 15, wherein said computer means is connected to automated means for maintaining the concentration of the chemical components of the aqueous phosphate conversion-coating bath at chosen concentrations.

18. A method for the quantitative analysis of chemical components of an aqueous phosphate conversion-coating bath, which method comprises:

purifying a sample of said aqueous phosphate conversion-coating bath to form a test fluid consisting essentially of an aqueous solution of ionic species;

determining the concentration of zinc ions present in said test fluid;

determining the concentration of phosphate ions present in said test fluid;

determining the pH of the test fluid;

determining the concentration of nitrite ions present in said test fluid; optionally, determining the concentration of fluoride ions present in said test fluid; and, optionally, determining the concentration of nickel ions present in said test fluid.

19. A method for the automatic, on-line quantitative analysis of chemical components of an aqueous phosphate conversion-coating bath, which method comprises the steps of:

automatically providing a sample of said aqueous phosphate conversion-coating bath to a purifying means by a conduit means, automatically purifying said sample to form a test fluid consisting essentially of an aqueous solution of ionic species; and automatically providing said test fluid by other conduit means to various determining means, and:

automatically determining the concentration of zinc ions present in said test fluid;

automatically determining the concentration of phosphate ions present in said test fluid;

automatically determining the pH of the test fluid;

automatically determining the concentration of nitrite ions present in said test fluid;

automatically carrying out said steps of said method by means of a computer; optionally, automatically determining the concentration of fluoride ions Present in said test fluid; and, optionally, automatically determining the concentration of nickel ions present in said test fluid.

20. An automated on-line detection system for quantitative analysis of chemical components of an aqueous phosphate conversion-coating bath, which automated on-line detection system comprises:

conduit means for providing a sample of said aqueous phosphate conversion-coating bath to an automated means for purifying said sample to form a test fluid consisting essentially of an aqueous solution of ionic species; and conduit means for providing said test fluid to:

automated means for determining the concentration of zinc ions present in said test fluid;

automated means for determining the concentration of phosphate ions present in said test fluid;

automated means for determining the pH of the test fluid;

automated means for determining the concentration of nitrite ions present in said test fluid; optionally, automated means for determining the concentration of nickel ions present in said test fluid; optionally, automated means for determining the concentration of fluoride ions present in said test fluid; and computer means for automating said detection system;

wherein (1) said automated means for determining said concentration of said zinc ions, (2) said automated means for determining said concentration of said nickel ions, and (3) said automated means for determining said concentration of said phosphate ions comprises X-ray fluorescence analysis.

21. The automated on-line detection system according to claim 20, wherein (1) said automated means for determining said pH, and said automated means for measuring said concentration of said fluoride ions comprises flow injection analysis employing specific ion electrodes, and (2) said automated means for determining said concentration of said nitrite ions comprises flow injection analysis employing colorimetric analysis techniques.

22. The automated on-line detection system according to claim 20, wherein said means for purifying said sample comprises an ultrafilter system.

23. An automated on-line detection system for quantitative analysis of chemical components of an aqueous phosphate conversion-coating bath, which automated on-line detection system comprises:

conduit means for providing a sample of said aqueous phosphate conversion-coating bath to an automated means for purifying said sample to form a test fluid consisting essentially of an aqueous solution of ionic species; and conduit means for providing said test fluid to:

automated means for determining the concentration of zinc ions present in said test fluid;

automated means for determining the concentration of phosphate ions present in said test fluid;

automated means for determining the pH of the test fluid;

automated means for determining the concentration of nitrite ions present in said test fluid;

automated means for determining the concentration of nickel ions present in said test fluid;

automated means for determining the concentration of nitrite ions present in said test fluid; and computer means for automating said detection system, wherein (1) said automated means for determining said concentration of said zinc ions, (2) said automated means for determining said concentration of said nickel ions, and (3) said automated means for determining said concentration of said phosphate ions comprises X-ray fluorescence analysis; wherein (1) said automated means for determining said pH, and said automated means for measuring said concentration of said fluoride ions comprises flow injection analysis employing specific ion electrodes, and (2) said automated means for determining said concentration of said nitrite ions comprises flow injection analysis employing colorimetric analysis techniques; and wherein said means for purifying said sample comprises an ultrafilter system.

* * * * *